US00RE47129E

(19) United States
(12) Reissued Patent
Shikani et al.

(10) Patent Number: US RE47,129 E
(45) Date of Reissued Patent: Nov. 20, 2018

(54) LOW PROFILE HEAT AND MOISTURE EXCHANGER DEVICE FOR TRACHEOTOMY AND SPEAKING VALVE

(71) Applicant: Shikani Medical, LLC, Lutherville, MD (US)

(72) Inventors: Alan H Shikani, Lutherville, MD (US); Frederick L. De Baugh, Lutherville, MD (US); James Thomas, Lutherville, MD (US)

(73) Assignee: SHIKANI MEDICAL, LLC, Forest Hill, MD (US)

(21) Appl. No.: 15/356,007

(22) Filed: Nov. 18, 2016

Related U.S. Patent Documents

Reissue of:
(64) Patent No.: 8,887,718
Issued: Nov. 18, 2014
Appl. No.: 13/199,525
Filed: Sep. 1, 2011

U.S. Applications:
(63) Continuation-in-part of application No. 12/928,648, filed on Dec. 16, 2010, now abandoned.

(51) Int. Cl.

| | |
|---|---|
| ***A62B 18/02*** | (2006.01) |
| ***A62B 9/02*** | (2006.01) |
| ***A61M 16/04*** | (2006.01) |
| *A61M 16/08* | (2006.01) |
| *A61M 16/10* | (2006.01) |

(52) U.S. Cl.
CPC ..... *A61M 16/0468* (2013.01); *A61M 16/047* (2013.01); *A61M 16/0434* (2013.01); *A61M 16/0497* (2013.01); *A61M 16/0816* (2013.01); *A61M 16/1045* (2013.01)

(58) Field of Classification Search
CPC ..... A16M 16/04; A16M 16/0402; A16M 16/0465; A16M 16/0468; A16M 16/10; A16M 16/1045; A16M 16/105; A16M 16/1075; A16M 16/1095; A16M 16/16; A16M 15/00; A16M 15/0005; A16M 2205/12; A16M 2205/152; A16M 2205/127; A16M 2205/128; A16M 2205/36; A16M 2205/362; A16M 2205/75; A16M 2205/7527; A16M 2205/7536; A61F 2/203; A62B 9/003
See application file for complete search history.

(56) References Cited

U.S. PATENT DOCUMENTS

| | | | | |
|---|---|---|---|---|
| 3,952,335 A * | 4/1976 | Sorce | A61F 2/203 128/207.16 |
| 4,141,703 A * | 2/1979 | Mulchi | 96/132 |
| 5,022,394 A | 6/1991 | Chmielinski | |

(Continued)

OTHER PUBLICATIONS

International Search Report for PCT/US2011/065625 dated Apr. 5, 2012.

(Continued)

*Primary Examiner* — Joseph Kaufman
(74) *Attorney, Agent, or Firm* — Hauptman Ham, LLP

(57) ABSTRACT

A heat moisture exchange device received on a speaking tube mounted on an end of a tracheotomy tube. The heat moisture exchange device has a housing in which the air moves in a turbulent manner and passes through a heat moisture exchange filter.

20 Claims, 11 Drawing Sheets

(56) References Cited

U.S. PATENT DOCUMENTS

| | | | | |
|---|---|---|---|---|
| 5,123,936 | A * | 6/1992 | Stone et al. | 95/65 |
| 5,460,172 | A * | 10/1995 | Eckerbom et al. | 128/201.13 |
| 5,592,933 | A * | 1/1997 | Zucchi | 128/201.13 |
| 5,992,413 | A | 11/1999 | Martin, Jr. et al. | |
| 6,921,417 | B2 * | 7/2005 | Persson | 623/9 |
| 2005/0178390 | A1 * | 8/2005 | Worthington | A61F 2/20 128/207.16 |
| 2006/0157056 | A1 | 7/2006 | Burk | |
| 2009/0301476 | A1 | 12/2009 | Korneff et al. | |
| 2013/0192602 | A1 * | 8/2013 | Leibitzki | A61M 16/0468 128/205.27 |

OTHER PUBLICATIONS

M.O. Carpinlioglu, M.Y. Gundogu. "A critical review on pulsatile pipe flow studies directing towards future research topics." Flow Measurement and Instrumentation 2001. 12: 163.

T.8. Zhao. P. Cheng. Experimental studies on the onset of turbulence and frictional losses in an oscillatory turbulent pipe flow . . . Int. J. Heat and Fluid Flow. 1996.

* cited by examiner

LOW PROFILE HEAT AND MOISTURE EXCHANGER DEVICE FOR TRACHEOTOMY AND SPEAKING VALVE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

[CROSS REFERENCE TO] RELATED APPLICATIONS

The present application *is a broadening reissue of U.S. patent application Ser. No. 13/199,525, filed Sep. 1, 2011, now U.S. Pat. No. 8,887,718, issued Nov. 18, 2014, which* is a continuation-in-part of patent application Ser. No. 12/928,648 filed Dec. 16, 2010, now abandoned the disclosure and contents of which are included by reference herein in their entirety.

BACKGROUND OF THE INVENTION

1. Field of the Invention

The present invention is directed to a heat moisture exchange device which is usable with a tracheotomy tube and a tracheotomy tube combined with a speaking valve.

Tracheotomy is a surgical procedure which is frequently performed to relieve obstruction of airflow through the larynx and upper trachea. One of its main side effects is loss of essential breathing functions including humidification, warming and filtering of air, coughing, smelling, tasting, swallowing, and more devastatingly, speaking. In tracheotomy patients, because inhaled air enters the trachea directly, it is very important for health reasons and for the patient's comfort, that the inhaled air is at substantially the same temperature and contains the same quantities of moisture and dust as if it had reached the trachea after passing through the upper airway (nostrils, nose, pharynx and larynx), meaning a temperature approaching 32° Celsius with a moisture content approaching saturation at the temperature of this air and substantially free of dust. HME's (Heat Moisture Exchanger) enable this result to be achieved to some degree; the filter mass blocks a major part of the dust in suspension in the air, of course, the water vapor contained in the patient's exhaled air, which is saturated at the temperature of the organism, condenses on the filter mass which is therefore heated substantially to the body temperature; inhaled air, arriving at the temperature of the ambient air, is warmed and takes up moisture in contact with the filter mass which is at a higher temperature and contains the condensed water before traveling into the patient's lungs with inhalation.

In order to overcome these undesirable side effects of a tracheotomy procedure, the passive HME was developed and has been available for many years. An HME consists of a housing to direct exhaled airflow from the patient, through one of many types of humidifying and moisturizing media. This device is placed externally in between the outside air and the patient's air intake at the tracheotomy tube. Exhaled air from the patient enters the HME, is directed across the media. The media serves to absorb and retain moisture from the exhaled air. On inspiration, humidified and warmed air is then breathed in by the patient, thus achieving some of the effect of the natural nasal passage. The ebb and flow of air across its surface allows a recurring transference of moisture from the patient's exhaled air to the HME and back to the patient. The HME's hence provide humidification warming and filtration of air that the tracheotomy patients breathe. The problem with the current HME's on the market is that because air flow inside them is linear, the exchange of humidity and warmth of the air that flows through the HME is not very efficient, hence a relatively large amount of HME foam material is needed, hence making the device quite bulky and unattractive to the patient. The present invention introduces a novel type of HME having a shape which is compact and designed to redirect airflow inside the HME in a turbulent fashion, hence enhancing the efficiency of humidification, warming and filtration of air.

Another problem is that because HME's moisturize and filter exhaled air, there is no one HME that can work with the speaking valves that are currently on the market because the valves are closed upon exhalation and do not allow air to pass. This invention addresses this issue and solves this problem by introducing an HME that works in combination with a speaking valve to allow both air moisturizing AND speech.

One additional significant situation that tracheotomy patients face is loss of speech. When a tracheotomy is present, exhaled air follows the path of least resistance, and goes through the tube, limiting the vibratory movement of the vocal cords, and hence limiting perceptual speech. This creates a psychological hardship, as communication is critical to patients' overall medical care and social interactions. This problem can be particularly disruptive in children, where tracheotomy can actually impact the development of normal language skills. In order to redirect the air through the vocal cords, the patient may use a finger to occlude the tracheotomy tube. Finger occlusion however has several limitations: it requires manual dexterity (which some patients may lack); it also requires coordination of phonation with breathing (which some patients may be unable to perform); and it is unsanitary. The use of a tracheotomy speaking valve enables tracheotomy patients to speak without having to occlude the tracheotomy tube with their finger. Unidirectional speaking valves have a displaceable element that allows air to flow through the cannula and into the lungs during inspiration and prevent air from flowing through the cannula during exhalation. Thus, during expiration, air flows through the patient's upper airways, such as the sub-glottic trachea, larynx, pharynx, mouth and nasal passages. As a result, unidirectional speaking valves allow tracheotomy individuals to communicate orally and maintain clear upper airway passages by coughing or expelling air through the upper airway passages.

The problem is that there is no one speaking valve currently on the market that can be used in combination with an HME's, the patient who use these speaking valves are unable to humidify/warm and filter the air that they inhale. This is due to the fact that the current speaking valves on the market are "biased closed", which means that, while they allow redirection of air towards the larynx during exhalation (and subsequent speech), they do NOT allow exhaled air to flow through the valve. This limitation places the tracheotomy patient in the unfortunate position of being able to speak with a speaking valve, but not being able to use an HME in order to humidify/warm and purify the breathed air. The object of this invention is to introduce an HME that can function in combination with a speaking valve and humidify/warm and purify the air that a tracheotomy patient breathes.

In the parent application, we have previously described a speaking valve with a ball that moves inside a chamber where eccentrically positioned ramps act as a stop mechanism and also act as a dynamic guide that directs the ball towards the front or the back of the chamber. The patient can vary the position of the valve (valve "up" or valve "down") by rotating it 180° up or down, and this allows the ball to be seated in the proximal part of the chamber either in the "biased open" or biased closed" position. This feature gives the patient control on the use of the valve to preferentially allow the exhaled air to escape through the proximal opening or redirect the air towards the larynx and speak.

The current invention is a continuation in part of the previous invention, extending the functionality of our previously described dynamic speaking (valve "up" or valve "down") (which allows "biased open" or "biased closed" usage) to be able to combine it with an HME for the sake of speech AND humidification, warming, and filtration of air.

2. Description of Related Art

A variety of one-way speaking valves has been described in the literature and is on the market. These include the Passy-Muir valve, the Shiley Phonate valve, the Kistner valve and the Montgomery speaking valve, and they operate via a flap or diaphragm. These "flapper" valves close on exhalation in order to provide speech; hence they cannot be used in combination with an HME. Prior U.S. Pat. No. 5,505,198 (Siebens et al) describes a unidirectional tracheotomy speaking valve with an external cylindrical housing chamber that contains a ball acting as the displaceable element. The ball moves back and forth during inspiration and expiration, and is limited from going beyond the housing chamber during inspiration by a pin or a wire that extends into the chamber and intersects a path of travel of the ball, preventing it from entering the patient's airway. In this patent, the housing chamber is external to the tracheotomy tube and attached to the cannula of a tracheotomy tube through coupling. U.S. Pat. No. 6,588,428 (Shikani et al) describes a similar design unidirectional speaking valve in which the housing chamber is internal and an integral part of the inner cannula of the tracheotomy tube, the ball is guided by longitudinal ribs and is restrained in the cannula by a wire.

While these ball valve patents constitute a substantial improvement in the art over the flapper valves, nevertheless, the fact that the valve housing chamber is a simple cylindrical tube that houses a ball that travels back and forth along the tube's central axis, with no guiding ribs that could potentially direct the movement of the ball depending on the orientation of the valve (valve "up" or "down"). This unidirectional ball speaking valve cannot be used in concert with an HME.

BRIEF SUMMARY OF THE INVENTION

The present invention provides an improved heat moisture exchange device for use with a tracheotomy tube and with a tracheotomy tube in concert with a speaking valve.

Eccentrically positioned ramps inside the chamber of the ball speaking valve act as a stop mechanism but also act as a dynamic guide that directs the ball towards the front or the back of the chamber, depending on the position of the valve (valve "up" or valve "down"). The eccentric ramps allow a method of using the speaking valve in two different positions, and providing a positive ball positioning feature depending how the housing chamber is rotated, hence greatly improving performance. In one mode, with the valve oriented "down", the ball is automatically held fully seated towards the front opening of the valve body, when the patient is breathing regularly at rest. This innovation allows the ball to sit inside the frontal opening and provide a leak free seal to the valve with no expiratory air required to seat the ball in the opening ("biased-closed position"). In the other mode with the valve oriented "up", the ball has a tendency to sit away from the frontal opening, closer to the posterior opening of the chamber, providing a more open airflow passage ("biased-open position") hence allowing the patient to breathe easier. Additionally, the ball now requires a conscious effort in terms of exhalation force, to seat the ball in the frontal hole and seal off airflow. Because of this, exhaled air can either be allowed to exit through the valve rather than being redirected through the patient's upper airway. Alternately, the patient can force the ball to seat when re-direction of airflow is desired for speech production.

In the "bias open" position, exhaled air flows freely through the valve, hence allowing the improved tracheotomy speaking valve to be coupled/effective with a new Heat Moisture Exchange (HME) filter that fits over the improved speaking valve as a cap, enabling the patient to breathe inhaled air that is at substantially the same temperature and containing the same quantities of moisture and dust as if it had reached the trachea after passing through the upper airway (nostrils, nose, pharynx and larynx).

It is an object of the present invention to provide a heat moisture exchange device which is usable with a tracheotomy tube combined with a speaking valve and also with a tracheotomy tube or a speaking valve.

In accordance with the teachings of the present invention there is disclosed a heat moisture exchange device comprising a housing adapted to be received on an end of a tracheotomy tube, wherein exhaled and inhaled air may move into and out of the housing. The housing has a domed frontal wall and circumferential walls depending from the domed frontal wall. A bottom circular panel is joined to the circumferential walls. A circular opening is formed in the bottom panel. A plurality of legs are connected to the bottom panel extending upwardly within the housing toward the domed frontal wall. The legs are substantially parallel to the circumferential walls. A plurality of spaced-apart openings are formed in the circumferential walls. Means are disposed within the housing to produce turbulent air flow within the housing. A heat and moisture exchange filter is mounted within the housing through which the air flows wherein moisture and heat from the exhaled air is transferred to the filter and inhaled air is heated and moisturized by the filter. Particulates in the air are collected by the filter.

The HME has a special design and shape that allows a more efficient exchange of heat and humidification and more efficient air filtration by making the air flow in a turbulent pattern inside the housing of the HME, rather than a linear pattern.

In addition, in accordance with the teachings of the present invention, there is disclosed a speaking valve for use with a tracheotomy device. A body has a proximate end and a distal end, respectively. The distal end of the cylinder has an opening formed therein. The body has a ramp means formed therein. A ball is disposed in the body between the ramp means and the opening and trapped therein. The ramp means includes a pair of substantially-parallel ramps spaced laterally apart a distance which is less than the diameter of the ball.

It also is the object of this invention to describe a method of using the HME with a dynamic ball speaking valve that can function either as "biased-closed" or "biased-open" depending on the orientation of the valve oriented (up or down).

These and other objects of the present invention will become apparent from a reading of the following specification taken in conjunction with the enclosed drawings.

DETAILED DESCRIPTION OF THE INVENTION

Figure 1:
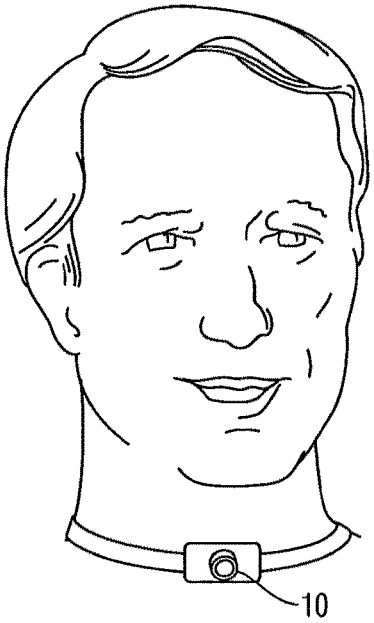
FIG. 1 is a perspective view showing a tracheotomy tube worn by a patient.
Figure 2:
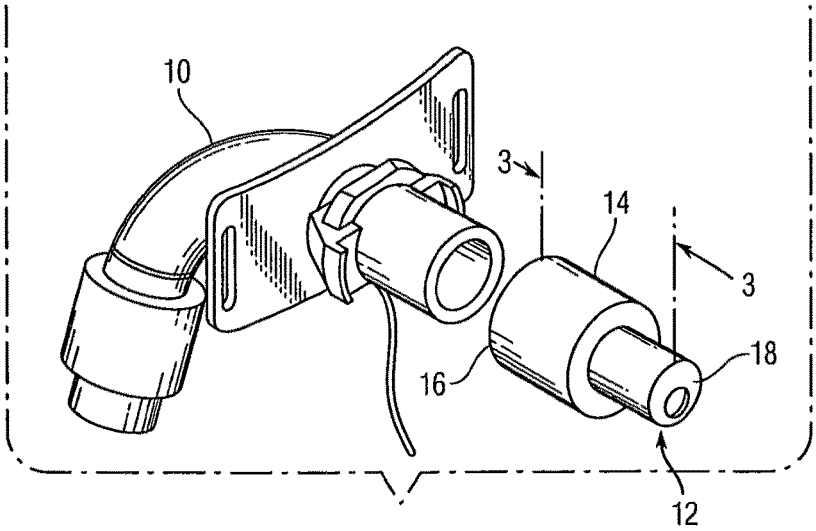
FIG. 2 is a perspective view of a tracheotomy tube with the valve of the present invention.

Referring to FIG. 1, a tracheotomy tube 10 is surgically implanted in the throat of a patient for airway management. On the end of the tracheotomy tube extending outwardly from the patient's throat at an angle of approximately 20°, there is removably-mounted the speech valve 12 of the present invention (FIG. 2).

Figure 3:
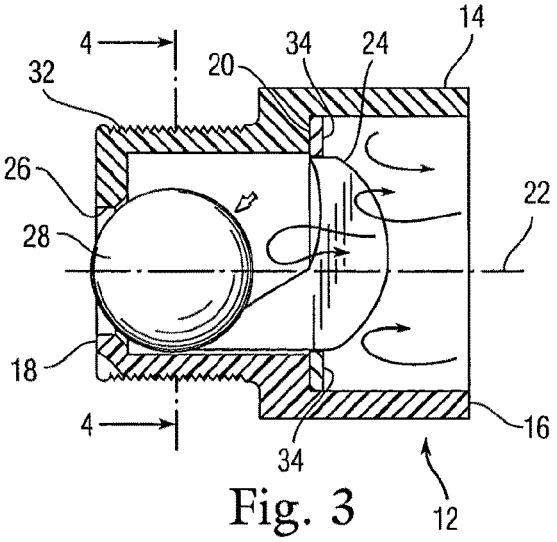
FIG. 3 is a cross-section taken along the lines 3-3 of FIG. 2 with the indexing means in a down position.
Figure 4:
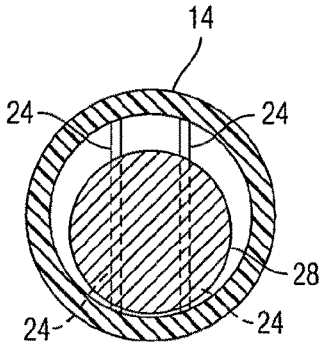
FIG. 4 is a cross-section view taken along the lines 4-4 of FIG. 3.
Figure 5:
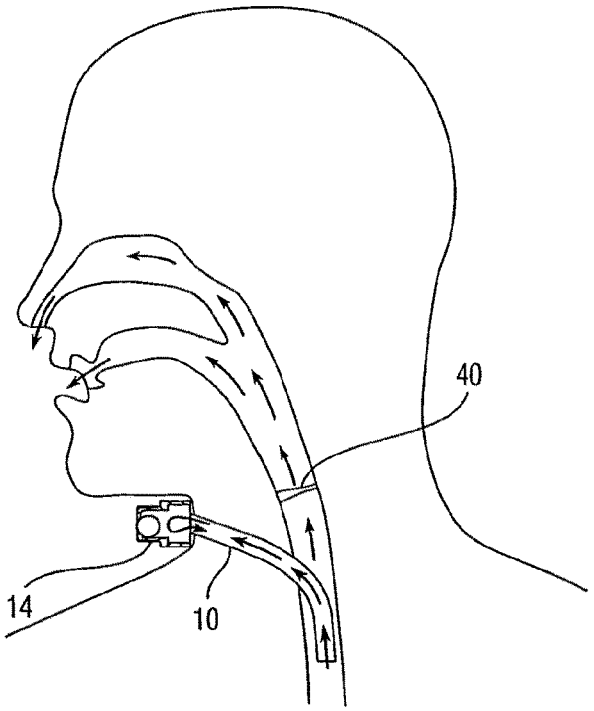
FIG. 5 is a partial cross-section view of the tracheotomy to be worn by the patient with the indexing means of the present invention in the down position and showing airflow when the patient stops inhaling.

The speech valve 12 has a body 14 with a first end 16 which communicates with the outer end of the tracheotomy tube 10. The diameter of the first end 16 of the body is larger than the diameter of the second end 18 of the body forming a chamber having an internal step 20 within the body 14 (as shown in FIG. 3). The first end of the body is open. The second end 18 of the body 14 has a frontal opening 26 formed therein which is offset from the central axis 22 of the body. Within the body are a plurality of circumferentially spaced ramps 24. A portion of each ramp slopes upwardly at an acute angle toward the first end of the body. Preferably, there are two parallel ramps 24, although more or fewer ramps may be used. Within the body, between the frontal opening 26 and the ramps 24, there is disposed a ball 28. The ball has a diameter which is larger than the diameter of the frontal opening 26 in the second end of the body. The ramps are spaced apart a distance which is less than the diameter of the ball 28 to retain the ball within the body 14. The ramps form a channel or guide to keep the ball along a midline axis 22, making movement of the ball less turbulent and more efficient. The ramps have a defined slope to hold the ball fully forward toward the frontal opening 26 as will be described. The direction of movement of the ball is shown by the open arrow. Thus, in an "in rest" position when the body 14 is in a desired approximately horizontal position, the ball 28 is automatically seated against the frontal opening 26, thereby sealing the frontal opening when the patient is neither inhaling nor exhaling (FIGS. 3-5). The air passageway in the patient's upper airway is open for the passage of air and air passes over the vocal cords 40 enabling the patient to speak.

There is an indexing means 30 formed on the second end 18 of the body which is used to determine the orientation of the body 14. The body may be rotated through 180° by the patient (or the patient's caregiver) to provide an "up" and a "down" position of the body. The outer surface of the body may have threads 32 or ribs formed thereon to provide a better grip to rotate the body.

Figure 16:
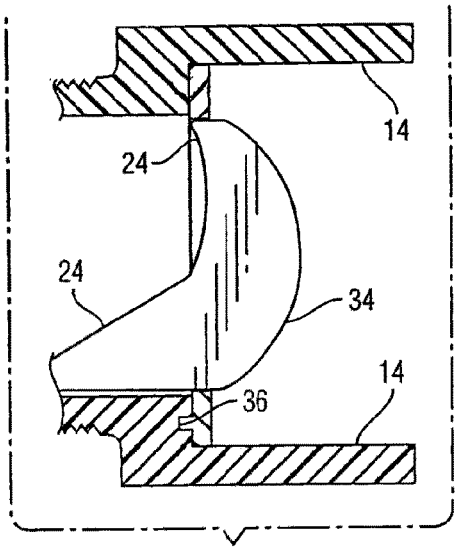
FIG. 16 is a cross-section view showing tab on the ring received in notch in the body.
Figure 17:
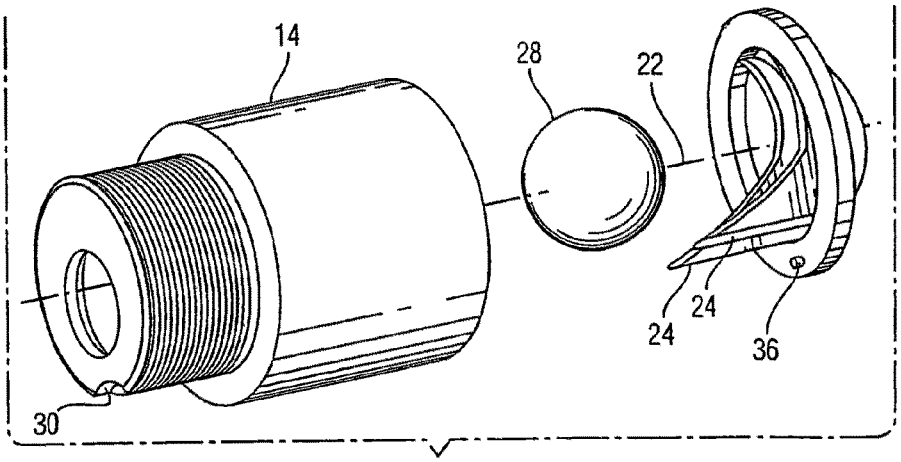
FIG. 17 is an exploded view of the valve of the present invention.
Figure 18:
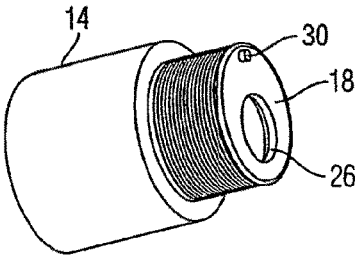
FIG. 18 is a perspective view showing a protrusion as the indexing means.
Figure 19:
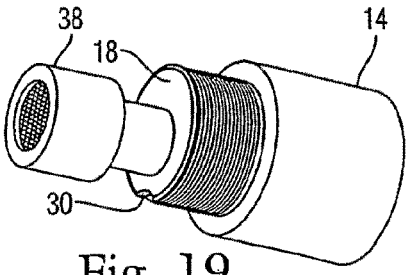
FIG. 19 is a perspective view showing a Heat Moisture Exchange attachment to the valve.

In a preferred embodiment the indexing means 30 is a notch or non-round portion of the second end of the body located near the frontal opening in the body. Alternately, as shown in FIG. 16, the indexing means may be a protrusion extending outwards from the second end of the body. Other indexing means known to persons skilled in the art may be used to provide an indexing means that may be sensed tactilely by the patient.

Figure 6:
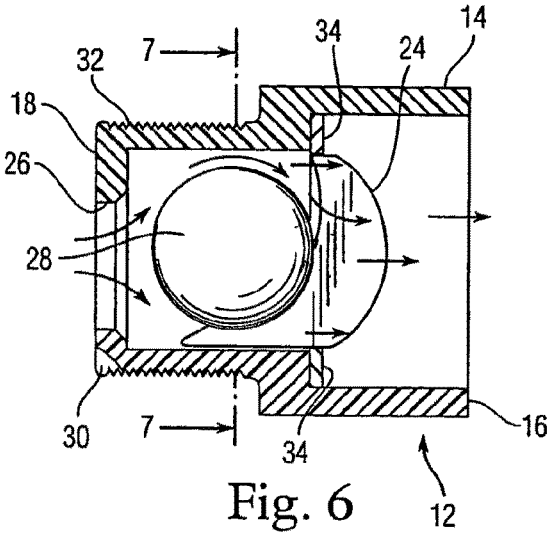
FIG. 6 is a cross-section view corresponding to the view taken across the lines 3-3 of FIG. 2.
Figure 7:
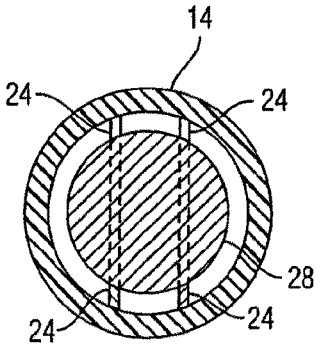
FIG. 7 is a cross-section view across the lines 7-7 of FIG. 6.
Figure 8:
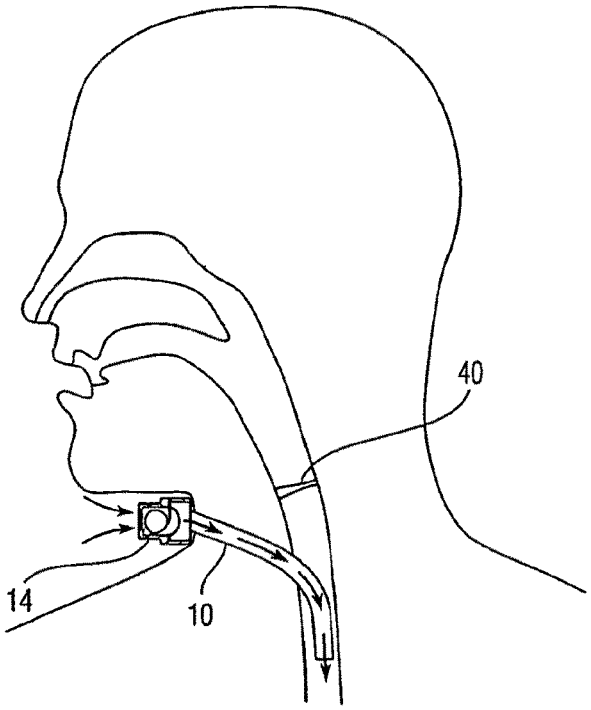
FIG. 8 is a partial cross-section view of the tracheotomy tube worn by the patient with the indexing means of the present invention in the down position showing airflow when the patient inhales.

As shown in FIGS. 6-8, when the indexing means in the "down" position, and the patient inhales, the incoming air moves the ball up the ramps 24 toward the tracheotomy tube 10 and air flows around the ball, between the ramps and into the patient's lungs.

With the indexing means in the "up"/biased-open position (FIGS. 9-11), and the patient in the resting position, the ball rests posteriorly in the chamber toward the tracheotomy tube, allowing free flow of air. As the patient inhales, incoming air flows over the ball, between the ramps, and into the patient's lungs.

Figure 12:
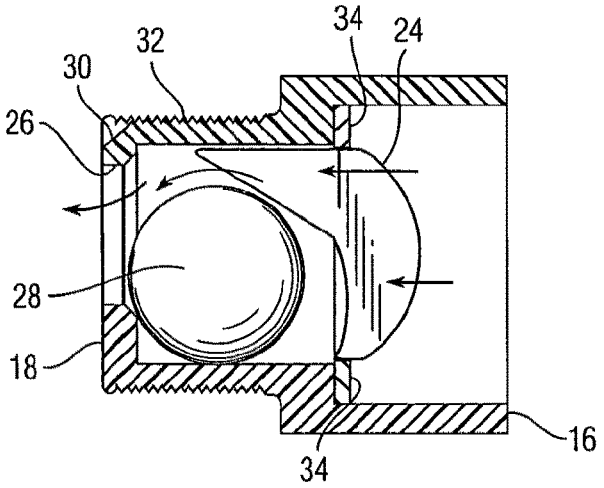
FIG. 12 is a cross-section view corresponding to the view taken across the lines 3-3 of FIG. 2, however, showing the indexing means in the up position when the patient exhales.
Figure 13:
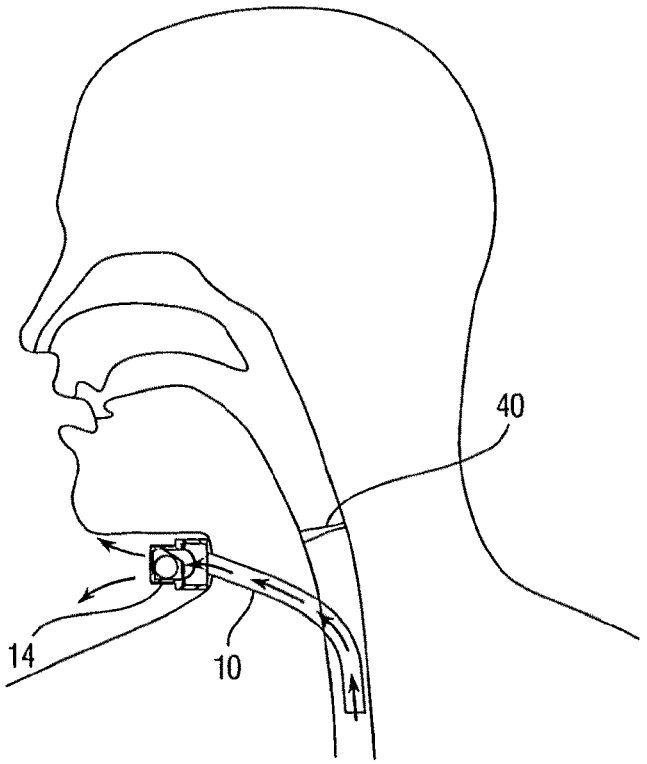
FIG. 13 is a partial cross-section view of the tracheotomy tube worn by the patient with the indexing means of the present invention in the up position showing airflow when the patient exhales.
Figure 14:
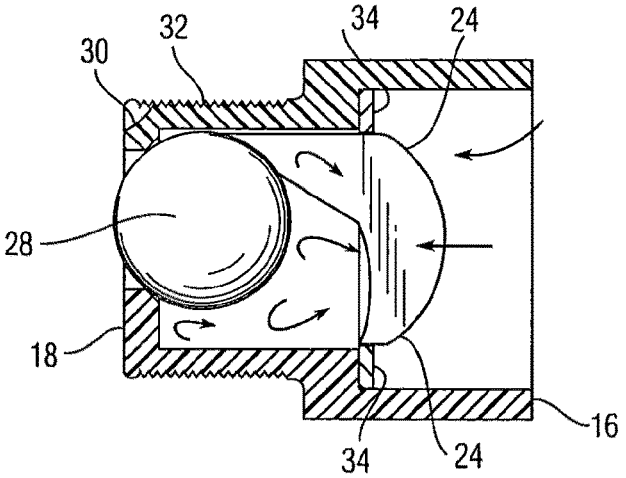
FIG. 14 is a cross-section view corresponding to the view taken across the lines 3-3 of FIG. 2, however, the indexing means is in the up position when the patient exhales with increased force.

With the indexing means in the "up" position, when the patient exhales (FIGS. 12 and 13), the ball is displaced toward the frontal opening but the ball does not rise upwardly to the eccentrically formed frontal opening which is near the upper portion of the body when in the "up" position. No seal occurs in the frontal opening and air moves out of the patient's lungs, through the tracheotomy tube, and exits out of the valve.

However, with the indexing means in the "up" position, if the patient increases the exhalation force, the ball is forced upwardly in the chamber and the ball seats in the frontal hole wherein air does not flow through the valve but the air is forced through the upper airway of the patient. In this scenario, the patient can speak since air is passing over the patient's vocal cords 40.

Thus, in a preferred embodiment, the present invention allows a method of using the speaking valve in two different positions ("up" or "down"), and providing a positive ball positioning feature depending on how the housing chamber is rotated, hence greatly improving performance. In the "down" mode the ball is automatically directed forward and held fully seated towards the front opening of the valve body, when the patient is breathing regularly at rest. This innovation allows the ball to sit inside the frontal opening and provide a leak free seal to the valve with no expiratory air required to seat the ball in the opening ("biased-closed position"). In the "up" mode, the ball has a tendency to sit away from the frontal opening, closer to the posterior opening of the chamber, providing a more open airflow passage ("biased-open position") hence allowing the patient to breathe easier. Additionally, the ball now requires a conscious effort in terms of exhalation force, to seat the ball in the frontal opening and seal off airflow. Because of this, exhaled air can either be allowed to exit through the valve rather than being redirected through the patient's upper airway. Alternately, the patient can force the ball to seal when re-direction of airflow is desired for speech production.

The ramps 24 are connected to a ring 34 which is disposed against the internal step 20 such that the ramps 24 extend inwardly into the chamber in the body 14. The ring 34 is keyed and ultrasonically welded to the step of the body to retain the ramps in place and in a proper orientation (FIG. 16). The keying means 36 may be a tab formed on the ring with a cooperating notch formed in the step, or the tab may be formed on the step and the notch may be formed on the ramp's ring. Other keying means known to persons skilled in the art may be used.

In an alternate mode, the valve including the body, the ramps and the ball, is mounted in the cannula of the tracheotomy tube. Although the valve cannot be rotated, the valve operates in a manner as described above.

Figure 9:
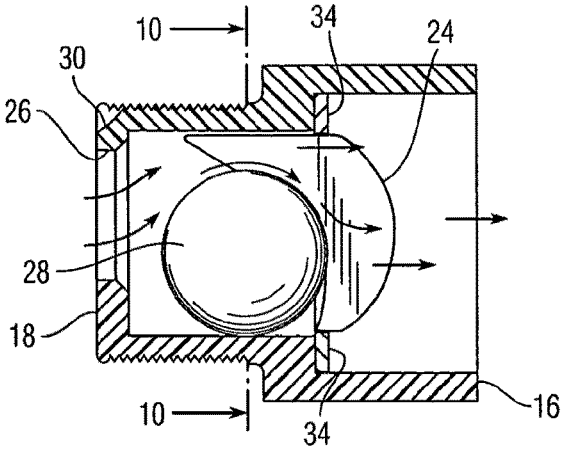
FIG. 9 is a cross-section view corresponding to the view taken across the lines 3-3 of FIG. 2, however, with the indexing means in the up position when the patient inhales.
Figure 10:
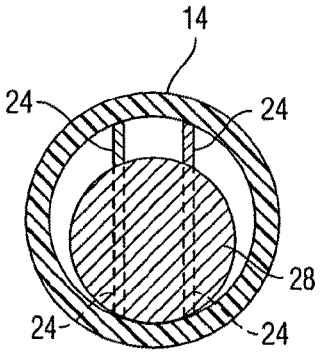
FIG. 10 is a cross-section view across the lines 10-10 of FIG. 9.
Figure 11:
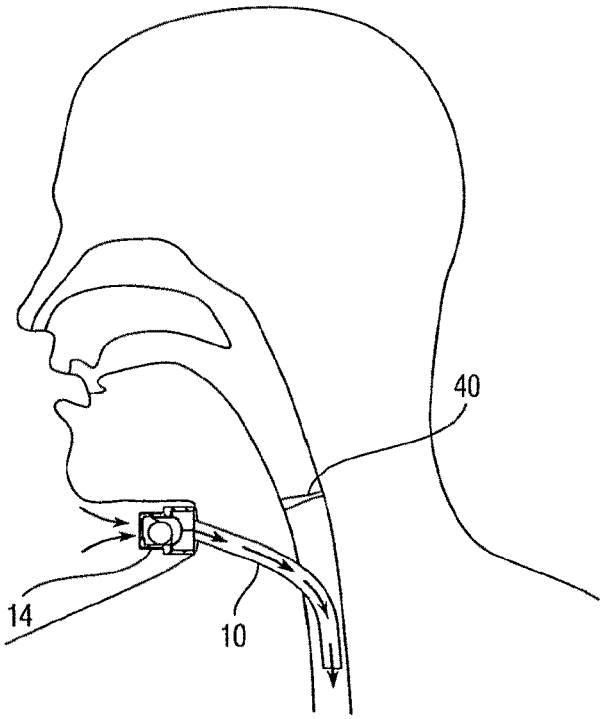
FIG. 11 is a partial cross-section view of the tracheotomy tube worn by the patient with the indexing means of the present invention in the up position showing airflow when the patient inhales.
Figure 15:
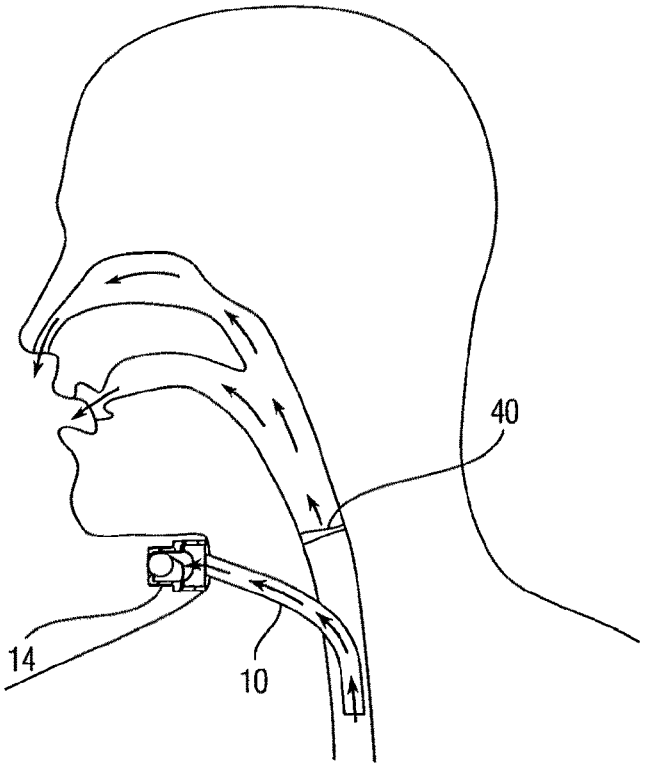
FIG. 15 is a partial cross-section view of the tracheotomy tube worn by the patient with the indexing means of the present invention in the up position showing airflow when the patient exhales with increased force.
Figure 20:
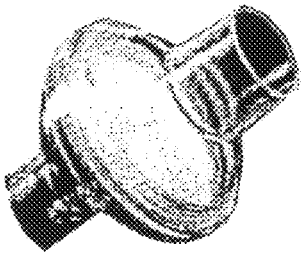
PRIOR ART FIG 20
FIG. 20 is a perspective view of a heat moisture exchange device of the prior art.
Figure 21:
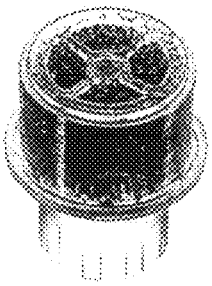
PRIOR ART FIG 21
FIG. 21 is a perspective view of another heat moisture exchange device of the prior art.
Figure 23:
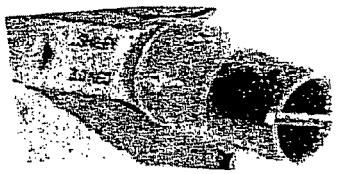
PRIOR ART FIG 23
FIG. 23 is a perspective view of a heat moisture exchange device of the prior art.
Figure 24:
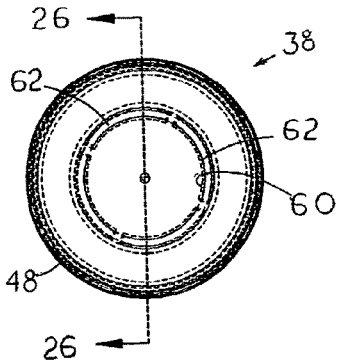
FIG. 24 is a bottom plan view of the present invention.

Having the exhaled air from the patient make contact with heat moisture exchange (HME) media is essential to the function of an HME. Because HME filters function only when air from the patient is exhaled across the media, and then returned to the patient, use of an HME is not possible with all other current unidirectional speaking valves which do not allow two-way airflow (air in and air out). Prior to the valve design of the present invention, patients had to choose either to wear a speaking valve for communication and forgo the benefit of an HME filter, or alternatively to wear an HME filter and forgo the benefits of wearing a speaking valve (FIGS. 20, 21 23). In the present invention a cap 38 containing fibers for HME is removably attached to the second end of the body. The novel ball valve's guiding design is unique in a sense that when the indexing means is in the "up" position (biased-open), the ball rests posteriorly inside the chamber, greatly facilitating airflow during inhalation (FIGS. 9, 10, 11). This position accommodates the use of an HME as follows. Upon exhalation, air is uniquely allowed to flow back out through the valve, and through the HME, making contact with the filter media. In this way the patient receives the benefit of the HME filtered air upon inspiration. However, with the valve in this same position, the patient can also choose to have the ball seat and seal at will, allowing redirection of the exhaled air over the vocal cords, in order to produce speech. No repositioning of the valve itself is necessary to achieve this. This is accomplished simply by providing increased expiratory volume in order to drive the ball forward and vertically up the frontal wall, and into the frontal opening to seat the ball and seal off airflow (FIG. 15).

This speaking valve uniquely allows the tracheotimized patient to realize the benefits of both automatic speech and humidification concurrently.

FIGS. 20, 21 and 23 show examples of HME's on the market, which are designed to be used directly over tracheotomy tubes (with or without the patient being on a ventilator). Having exhaled air from the patient make contact with the HME media is essential to the function of an HME, because HME filters function only when air from the patient is exhaled across the media, and then returned to the patient.

Figure 22:
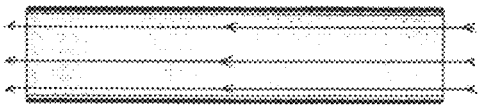
FIG. 22 is a schematic drawing showing linear air flow through the heat moisture exchange media.

Current HME's on the market provide humidification and heat exchange as the inhaled/exhaled air flows through the HME device in a linear fashion (see FIG. 22).

The current designs resort to a large frontal area for sufficient media volume to achieve humidification, with the resulting bulkiness, increased weight and size, making them uncomfortable and unappealing to patients hence limiting their clinical acceptance (see FIG. 23).

In the present invention, a housing 42 is adapted to be received on an end of a tracheotomy tube 10 wherein exhaled and inhaled air may move into and out of the housing. The housing has a domed frontal wall 46. A bottom circular panel 58 is joined to the circumferential walls 48. A circular opening 60 formed centrally in the bottom panel 58. A plurality of legs 62 are connected to the bottom panel 58, the legs extending upwardly within the circular opening 60 toward the domed frontal wall 46. The individual legs 62 are separated from the adjoining leg 62 by a narrow slit wherein the legs have a degree of flexibility. The legs 62 are substantially parallel to the circumferential walls 48.

A plurality of spaced-apart openings 50 are formed in the circumferential walls 48. Dead space 52 is formed within the housing 42, preferably bounded by the domed frontal wall 46.

A filter media 54 is formed as a sheet which is disposed completely around the housing between the interior of the circumferential wall 48 and the legs 62 extending upwardly from the bottom panel 58. In this manner the filter media covers all of the spaced-apart openings 50 so that air moving into or out of the housing must traverse the filter media. It has been found that porous reticulated ester-type polyurethane foam having a pore size of 65 pores per inch is satisfactory in the present invention. This is not a limitation on the filter media and other types of foam with other pore sizes may be used. Pore sizes are available from 40 ppi to 90 ppi with 50 ppi to 70 ppi being most common. The filter media may not be a foam but could be a filter paper. The filter media is impregnated with a hygroscopic material. Calcium chloride has been found to be a satisfactory hygroscopic material.

Figure 26:
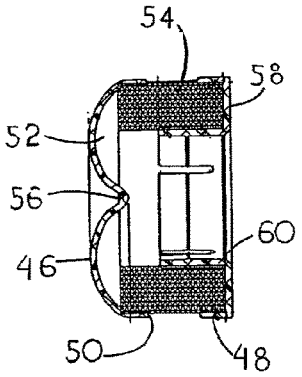
FIG. 26 is a cross section view taken across the lines 26-26 of FIG. 24.
Figure 27:
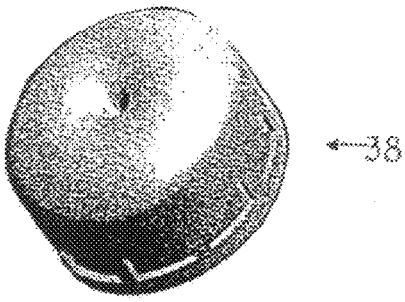
FIG. 27 is a top perspective view of the present invention.
Figure 28:
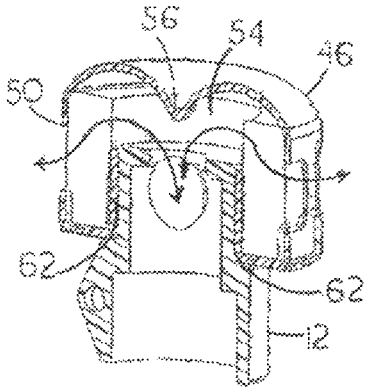
FIG. 28 is a cross sectional view showing air movement into and out of the housing.
Figure 31:
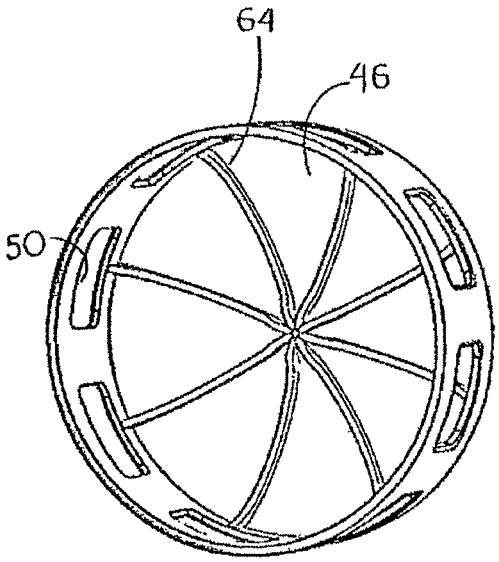
FIG. 31 is a bottom perspective view showing vanes within the cap to produce turbulent air movement.

The effectiveness of the present invention is enhanced by producing nonlinear turbulent air flow within the housing. A dimple 56 formed centrally, interiorly of the domed frontal wall 46 is an effective means to produce turbulence (FIGS. 26-28). The turbulence assures good humidification and heat transfer of the air as it passes through the filter. Other means to produce turbulence in the air movement within the housing such as vanes 64 within the housing may be used (FIG. 31). However, the turbulence must not be excessive so as to produce resistance to air flow.

The filter also removes particulates from the air. This is very important for a patient having a tracheotomy tube because the normal filtering by the nasal passages is not available.

Figure 25:
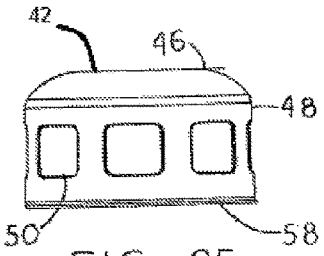
FIG. 25 is a side elevation view of the present invention.

The present invention is a new low-profile, high-performance heat moisture exchange device 42, based on air recirculation (turbulent air flow rather than linear airflow). This new compact HME takes advantage of its smaller size, and uniquely discrete profile design to maintain a very low visual profile (FIGS. 25, 27). It sits like a cap over the tracheotomy cannula 10 or the speaking valve 12 (FIGS. 25, 27). The HME has a diameter of approximately 1 inch and a height of approximately ⅝ inch. In addition, this HME incorporates unique design elements for optimal and efficient air flow and while maintaining a high level of humidification and heat transfer.

Air flows from the trachea (through the tracheotomy tube and/or the speaking valve) and gets redirected from the center of the HME when it encounters the dimpled/curved section in the center of the frontal wall 46. The airflow is directed towards multiple smaller openings 56 that are located on the side walls 48 and/or the bottom walls 52 of the HME housing 10 (FIGS. 25, 26, 27). This recirculation of air promotes flow instability and transition to turbulence, which intensity will increase with the speed of airflow. Turbulent flow, which may naturally occur within the lungs, is chaotic and involves multiple irregular eddies currents (circular currents) of air of many different length scales. When flow is turbulent, particles exhibit additional transverse motion, which results in increased rates of mass, momentum and heat exchange.

The enhancement of heat and momentum transfer is frequently expressed in terms of turbulent transport rates, namely according to:

$$q = -k_{turb}\frac{\partial \overline{T}}{\partial y}$$

$$\tau = \mu_{turb}\frac{\partial \overline{u}}{\partial y}$$

where q is the heat flux, $\tau$ is the shear stress, $\overline{T}$ is the mean temperature field, $\overline{u}$ is the mean velocity, $\mu_{turb}$ is the turbulent viscosity and $k_{turb}$ is the turbulent thermal conductivity. The enhanced transport arising in turbulent flow is directly linked to the fact that the turbulent viscosity and thermal conductivity are substantially larger than the molecular viscosity and thermal conductivity. Thus, with the same mean gradients, the turbulent transport rates are substantially larger than the corresponding laminar rates.

As discussed below, it is advantageous to conceive HME filter so that transitional and/or turbulent flow occurs during part or all the breathing cycle. The onset of turbulence can be characterized in terms of the oscillating Reynolds number $$R_{os} = \frac{UD}{\nu}$$

where U is the amplitude of the cross-sectional mean velocity, D is the diameter (or alternatively the so-called hydraulic diameter), and $\nu$ the kinematic viscosity of the fluid. Specifically, turbulence occurs when the $R_{os}$ exceeds a critical value, which may depend on the reduced frequency:

$$\omega' = \frac{2\pi D^2}{4\nu T}$$

where T is the fundamental period of the oscillations, and D is the hydraulic radius. (M. O. Carpinlioglu, M. Y. Gundogu, "A critical review on pulsatile pipe flow studies directing towards future research topics," Flow Measurement and Instrumentation 2001, 12:163-174, Elsevier Press. T. S. Zhao, P. Cheng, "Experimental studies on the onset of turbulence and frictional losses in an oscillatory turbulent pipe flow,", Int. J. Heat and Fluid Flow, 1996, 17:356-362, Elsevier Press). Correlations for the critical Reynolds number, $R_{os.crit}$, are readily available; for instance:

$$R_{os,crit}=780\sqrt{\omega'},\ 2.3\leq\sqrt{\omega'}\leq 8.8$$

$$R_{os,crit}=710\sqrt{\omega'}\ 4.0\leq\sqrt{\omega'}\leq 40.0$$

$$R_{os,crit}=400\sqrt{\omega'}\ 42.0\leq\sqrt{\omega'}\leq 71.0$$

Thus, the above expressions may be used to ensure that the HME filter includes one or more channels whose dimensions result in supercritical Reynolds number. In one embodiment of this invention, the HME filter is thus designed to operate in a regime where the flow has a supercritical Reynolds number.

In other embodiment of this invention, the critical Reynolds number for a specific design of the HME filter is determined experimentally. For instance, it is well known that when transition to turbulence occurs, the cycle averaged friction factor $\overline{C}_f$ changes from having an essentially inverse dependence on the Reynolds number, to being essentially Reynolds-number independent. The cycled averaged friction factor may be readily obtained from the instantaneous pressure drop, which may be measured using mechanical or piezoelectric pressure gauges.

Figure 29:
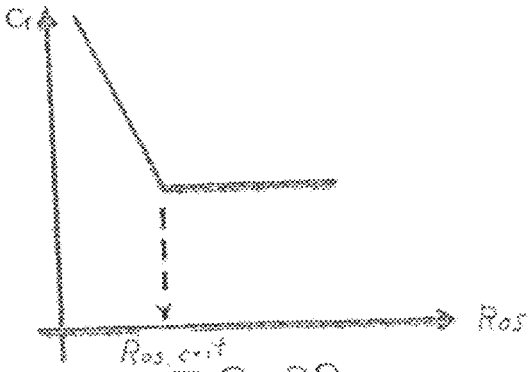
FIG. 29 is a graphical depiction of friction factor vs. critical Roswell member.

Thus, in one embodiment of this invention, a family of prototypes is evaluated. For each prototype the cycle-averaged friction factor is measured, and the measured values are plotted against $R_{os}$ (FIG. 29). When a logarithmic scale is used, the cycle-averaged friction factor would exhibit a branch with a −1 slope at low Reynolds number, and a second branch that is essentially flat at high Reynolds number. The critical Reynolds number, $R_{os,crit}$, may then simply be determined as the intersection of these two branches.

Thus, in one embodiment of this invention, the HME filter is designed to operate in a flow regime where the Reynolds number is above the critical value determined experimentally above.

An effective approach to control the Reynolds number is to consider the effect of the hydraulic diameter, D, on $R_{os}$. Specifically, $R_{os}$ may be related to the flow rate amplitude, Q, the diameter, D, and the kinematic viscosity, ν, by:

$$R_{os} = \frac{Q}{4\pi D\nu}$$

Thus, for fixed flow rate amplitude, Q, the Reynolds number increases as D decreases. In other words, the Reynolds number, $R_{os}$ may be increased by reducing the size of contractions or throats in the HME filter. It should be clear for someone skilled in the art how to extend this approach to achieve similar effects, namely by altering sizes or shapes of HME filters disclosed herein. In testing where Q is a fixed flow amplitude of 0.51/s, D is 4.2 mm and ν is 16 E −06 $m^2$/sec, the device operates at $R_{os}$ greater than approximately 600. One or more of the flow cross sections has a hydraulic diameter that is less than 5 mm.

This unique dimpled design was evaluated using HME performance tests according to ISO 9360-2: 2009 standard with 3 h runtime and test condition 8 (Vt=500 mL, rate=15/min). The test equipment used was certified and maintained in accordance with industry standards according to ISO 13485.

The design was tested according to these conditions and the results noted. The volume of media contained in this HME was measured. The same volume of media was tested according to the ISO 9360-2:2009 standard, using the same calibrated and certified test equipment, but in a "straight through" configuration per FIG. 22. The same volume of identical foam material was used in the tests.

Percent HME water loss (turbulent flow design):

A.1 15 mm Half 16.6 mg/L moisture LOSS=27.4 mg/L moisture RETURNED.

A.2 15 mm Half 17.0 mg/L moisture LOSS=27.0 mg/L moisture RETURNED.

Comparison HME media (linear flow design)

Linear Sample #1 21.0 mg/L moisture LOSS=23.0 mg/L moisture RETURNED.

Linear Sample #2 18.7 mg/L moisture LOSS=25.3 mg/L moisture RETURNED.

Comparing the 23.0 mg/l return of the linear design to the 27.4 mg/l return of the dimple design, the dimpled housing design showed an increase of 19% in efficiency for moisture output to the patient, as compared to the straight through design using identical media volume and test conditions. The only variable in the comparison tests were the shape of the housing. All other conditions were held identical.

This would indicate that the unique shape, with its increased contact time, increased in friction and more complex air currents and eddies resulted in an increase in moisture output. This translates to increased effectiveness and physiological benefit for the patient.

Figure 30:
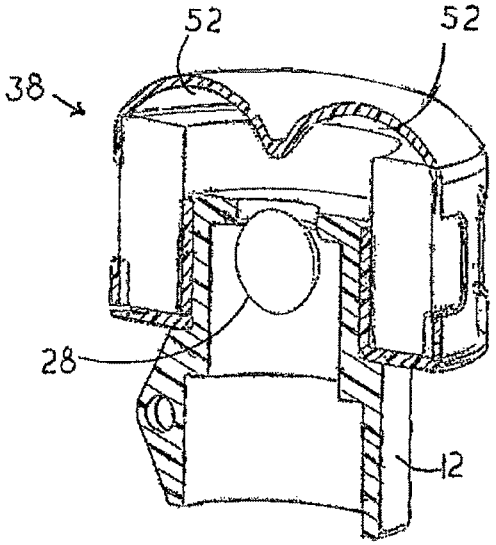
FIG. 30 is a cross sectional view of the housing mounted on the speech valve showing the dead space area.

The domed frontal wall 46 provides additional dead space/volume 52 within the small profile of this HME. The dead space affects the cross section of the area through which air flows, and further slows down airflow, hence resulting in enhancement of humidification and heat transfer (FIG. 30).

Air flow is affected by different factors including: 1. the cross-sectional area of the airway (which determines resistance); 2. nature of airflow (turbulent vs. laminar); 3. Reynolds' number (which depends on the density of the media through which air flows); 4. presence of dead space, and 5. the breathing effort by the patient (see below).

In one embodiment of this invention, the HME filter comprises passageways where the cross-sectional area changes rapidly. It is well known that when a stream is forced over such step or expansion, the flow separates which results in the generation of a recirculating region in the wake of the step or expansion region. Recirculating flow regions serve as effective reservoirs of heat and humidity, which benefits the operation of the device and ultimately the patient.

The heat and exchange moisture media preferably consists of reticulated ester-type polyurethane foam with a nominal porosity of 65 ppi (pores per inch). The material is die-cut into a hollow cylinder and subsequently treated with an aqueous solution of pharmaceutical grade calcium chloride. Other hygroscopic materials may be used. The foam is disposed internally in the housing such that air entering or leaving the spaced-apart openings in the housing must pass through the foam.

Having exhaled air from the patient make contact with the HME media is essential to the function of an HME. Because HME filters function only when air from the patient is exhaled across the media, and then returned to the patient, use of an HME is not possible with any of the other unidirectional speaking valves currently on the market, as they do not allow two-way air flow. Prior to this valve design, patients had to choose either to wear a speaking valve for communication and forgo the benefit of an HME filter, or alternatively to wear an HME filter and forgo the benefits of wearing a speaking valve. The novel ball valve's guiding design is unique in a sense that when the housing is in the "notch up" position, the ball sits back toward the retention tabs greatly facilitating air flow inhalation (ball is in "biased-open" position). This position accommodates the use of an HME as follows. Upon exhalation, air is allowed to flow back out through the valve, and through the HME when attached. In this way the patient receives the benefit of the HME filtered air upon inspiration. However, with the valve in this same position, the patient can also choose to have the ball seat and seal, allowing redirection of the exhaled air over the vocal cords, in order to produce speech. This is accomplished simply by providing increased expiratory volume in order to drive the ball forward and vertically up the frontal wall, and into the frontal opening to seat and seal off air flow. When the patient decides to give preferential priority to speech, rather than humidification, all that needs to be done is to rotate the valve 180 degrees and the ball moves forward towards the frontal opening (ball is in "biased-closed" position). This allows the patient to realize the benefits of either speech or humidification (FIG. 8).

What is claimed is:

1. A heat moisture exchange device comprising a housing adapted to be received on an end of a tracheotomy tube, wherein exhaled and inhaled air may move into and out of the housing, the housing having a domed frontal wall and circumferential walls depending from the domed frontal wall, a bottom circular panel joined to the circumferential walls, a circular opening formed in the bottom panel, the domed frontal wall having a dimple extending toward the circular opening, a plurality of spaced-apart legs connected to the bottom panel and extending upwardly within the housing toward the domed frontal wall, the legs being substantially parallel to the circumferential walls, a plurality of spaced-apart openings formed in the circumferential walls, and a heat and moisture exchange filter mounted within the housing through which air flows, wherein moisture and heat from the exhaled air is transferred to the filter and inhaled air is heated and moisturized by the filter and wherein particulates in the inhaled air are collected by the filter.

2. The heat [and] moisture exchange device of claim 1, wherein a speaking valve is mounted on the end of the tracheotomy tube and the heat moisture exchange device is mounted on the speaking valve wherein a patient fitted with the tracheotomy tube, the speaking valve and the heat and moisture exchange device may breathe and speak.

3. The heat moisture exchange device of claim 2, wherein the speaking valve comprises:

a plurality of ramps extending upward at an acute angle towards a first end of the speaking valve;

an opening at a second end of the speaking valve, wherein the opening is offset from a central axis extending from the first end to the second end of the valve; and a ball disposed between the opening and the plurality of ramps, wherein a diameter of the ball is greater than a diameter of the opening.

4. The heat moisture exchange filter of claim 1, wherein the filter is a filter material impregnated with a hygroscopic material.

5. The heat moisture exchange device of claim 1, wherein the filter material is a porous foam having multiple pores, each pore having a nominal pore size of approximately 65 ppi.

6. The heat moisture exchange device of claim 5, wherein the porous foam comprises ester-type polyurethane.

7. The heat moisture exchange device of claim 1, wherein

[a] *the* dimple is formed centrally on the domed frontal wall, the dimple *being* arranged to produce turbulence in [movement of] air *moving* within the housing.

8. A method of using the heat moisture exchange device of claim 1 *comprising:*

[with a tracheotomy tube wherein] *mounting* the heat moisture exchange device [is mounted] on the end of the tracheotomy tube and

[controls] *controlling* the temperature and moisture content of the air being inhaled and exhaled through *the mounted heat moisture exchange device and* the tracheotomy tube.

9. A heat moisture exchange device comprising a housing adapted to be received on a speaking valve which is mounted on an end of a tracheotomy tube in a patient fitted with the tracheotomy tube, wherein air may move into and out of the housing, the housing having a domed frontal wall and circumferential walls depending from the domed frontal wall, a bottom [circular] panel joined to the circumferential walls, a circular opening formed in the bottom panel, a plurality of spaced-apart legs connected to the bottom panel and extending upwardly within the housing toward the domed frontal wall, the legs being substantially parallel to the circumferential walls, a plurality of spaced-apart openings formed in the circumferential walls, means *for modifying air flow* disposed within the housing to produce nonlinear turbulent air flow within the housing, a heat and moisture exchange filter mounted within the housing between the legs and the openings in the [circumferentially] *circumferential* walls through which air flows, wherein moisture and heat from the exhaled air is transferred to the filter and inhaled air is heated and moisturized by the filter and wherein particulates in the inhaled air are collected by the filter, *and* wherein the means [disposed within the housing to produce nonlinear turbulent airflow within the housing] *for modifying air flow* is a dimple formed on the domed frontal wall extending towards the circular opening.

10. The heat moisture exchange filter of claim 9, wherein the filter is a filter material impregnated with a hygroscopic material.

11. The heat moisture exchange device of claim 9, wherein the [means to produce nonlinear turbulent air flow within the housing is the] dimple *is* formed centrally on the domed frontal wall.

12. The heat moisture exchange device of claim 9, wherein the turbulence is expressed as $$R_{os} = \frac{Q}{4\pi D v}$$

where Q is a fixed flow amplitude, D is a generic diameter of the heat moisture exchange device and ν is the kinematic viscosity of air and the device operates at $R_{os}$ greater than approximately 600.

13. The heat moisture exchange device of claim 12, wherein one or more flow cross sections have a hydraulic diameter that is less than 5 mm.

14. A method of using the heat moisture *exchange* device of claim 9 *comprising*

[with] *mounting the heat moisture exchange device on* the speaking valve, and

[tracheotomy tube wherein the heat moisture exchange device controls] *controlling* the temperature and moisture content of the air being inhaled and exhaled through *the mounted heat moisture exchange device and* the tracheotomy tube [and wherein] *as* the patient [may breathe and speak] *breathes and speaks*.

15. A heat moisture exchange device comprising:

a housing configured to be received on an end of a tracheotomy tube, the housing having a domed frontal wall, wherein the domed frontal wall has a dimple;

sidewalls extending downward from the domed frontal wall, wherein the sidewalls are perforated;

a panel connected to a distal portion of the sidewalls;

a plurality of legs extending from the panel toward the domed frontal wall; and a filter within the sidewalls of the housing;

wherein the dimple [is extending] *extends* in the same direction as the sidewalls.

16. The heat moisture exchange device of claim 15, wherein the filter is a porous foam having a plurality of pores, wherein each of the plurality of pores range from 40 ppi to 90 ppi.

17. The heat moisture exchange device of claim 16, wherein the porous foam comprises ester-type polyurethane.

[18. The heat moisture exchange device of claim 15, wherein the filter comprises a hygroscopic material.]

[19. The heat moisture exchange device of claim 15, wherein the filter comprises calcium chloride.]

[20. The heat moisture exchange device of claim 15, wherein the housing has a diameter of 1 inch.]

*21. The heat moisture exchange device of claim 2, wherein the speaking valve further comprises:*

*a body configured for being attached to and rotatable relative to the tracheotomy tube between a biased-closed position and a biased-open position, the biased-open position being 180° offset from the biased-closed position, the body having*

*a first end configured for communicating with the tracheotomy tube,*

*a second end distal from the tracheotomy tube configured for communicating with the heat and moisture exchange device,*

*a cylindrical chamber extending from the second end, and*

*an opening formed in the second end offset from a central axis of the chamber;*

*a ball disposed within the chamber, the ball having a diameter greater than the opening; and*

*a plurality of guides disposed within the cylindrical chamber and arranged for guiding movement of the ball within the chamber between a first position and a second position;*

*wherein, when the body is rotated to the biased-closed position, the guides have a first region configured and positioned to urge the ball toward and substantially close the opening, and*

*wherein, in response to a sufficient inhalation flow, the guides have a second region configured and positioned to urge the ball toward a substantially central position within the chamber and thereby define a generally annular flow passage.*

*22. The heat moisture exchange device of claim 21, wherein,*

*when the body is rotated to the biased-open position, the guides guide the ball to an offset position within the chamber whereby the opening remains substantially unobstructed, and*

*wherein, in response to a sufficient inhalation flow, the guides urge the ball toward a substantially rearward position within the chamber.*

*23. A speaking valve comprising:*

*a body having*

*a first end configured for being removably attached to a tracheotomy tube;*

*a second end configured for receiving a removably attached heat and moisture exchange device,*

*the body further being rotatable relative to the tracheotomy tube between a biased-closed position and a biased-open position, the biased-open position being 180° offset from the biased-closed position, the body having*

*a cylindrical chamber extending from the second end, and*

*an opening formed in the second end offset from a central axis of the chamber;*

*a ball disposed within the chamber; and*

*a plurality of guides disposed within the cylindrical chamber and arranged for guiding movement of the ball within the chamber between a first position and a second position;*

*wherein, when the body is rotated to the biased-closed position, the guides have a first region configured and positioned to urge the ball toward and substantially close the opening, and*

*wherein, in response to a sufficient inhalation flow, the guides have a second region configured and positioned to urge the ball toward a substantially central position within the chamber and thereby define a generally annular flow passage.*

* * * * *